US008951262B2

(12) United States Patent
Kecman et al.

(10) Patent No.: US 8,951,262 B2
(45) Date of Patent: Feb. 10, 2015

(54) PATELLA CLAMP AND DRILL GUIDE SURGICAL INSTRUMENT (75) Inventors: Maja Kecman, London (GB); Richard A. Hartshorn, London (GB); Edward H. Goodwin, London (GB); Abraham P. Wright, Winona Lake, IN (US); Kyle B. Thomas, Denver, CO (US); Duncan G. Young, Hebden Bridge West (GB); Lisa M. Stroux, Oxford (GB)

(73) Assignee: DePuy (Ireland) (IE)

( * ) Notice: Subject to any disclaimer, the term of this patent is extended or adjusted under 35 U.S.C. 154(b) by 305 days.

(21) Appl. No.: 13/538,086

(22) Filed: Jun. 29, 2012

(65) Prior Publication Data
US 2013/0023890 A1    Jan. 24, 2013

Related U.S. Application Data (60) Provisional application No. 61/503,419, filed on Jun. 30, 2011.

(51) Int. Cl.
A61B 17/17    (2006.01)
A61B 17/56    (2006.01)

(52) U.S. Cl.
CPC .................................. *A61B 17/1767* (2013.01)
USPC ............................................. 606/96; 606/99

(58) Field of Classification Search
USPC .......... 606/58, 86 R, 87–88, 96–98, 105, 282
See application file for complete search history.

(56) References Cited

U.S. PATENT DOCUMENTS

| 2,181,746 | A |   | 11/1939 | Siebrandt |
| 3,835,849 | A |   | 9/1974  | McGuire |
| 4,194,861 | A | * | 3/1980  | Keller ........................... 408/109 |
| D260,927  | S |   | 9/1981  | Glenn |
| D281,622  | S |   | 12/1985 | Diamond |
| 4,565,192 | A |   | 1/1986  | Shapiro et al. |
| 4,633,862 | A |   | 1/1987  | Petersen |
| 4,692,073 | A |   | 9/1987  | Martindell |
| 5,002,547 | A |   | 3/1991  | Poggie et al. |
| 5,021,055 | A |   | 6/1991  | Burkinshaw et al. |
| 5,108,401 | A |   | 4/1992  | Insall et al. |
| 5,116,338 | A |   | 5/1992  | Poggie et al. |
| 5,129,907 | A |   | 7/1992  | Heldreth et al. |

(Continued)

FOREIGN PATENT DOCUMENTS

EP    791335 A1    8/1997
EP    0992222 A2   4/2000

(Continued)

OTHER PUBLICATIONS

Depuy International, Ltd., PFC Sigma Rotating Platform Knee System With MBT Tray, Surgical Technique Brochure, 2003 (43 Pages), Cat. No. 9068-96-000, Depuy International, Ltd., Leeds, England.

(Continued)

*Primary Examiner* — Nicholas Woodall
*Assistant Examiner* — Larry E Waggle, Jr.
(74) *Attorney, Agent, or Firm* — Barnes & Thornburg LLP (57) ABSTRACT

An orthopaedic surgical instrument includes a patella drill guide having a first bracket, a second bracket coupled to the first bracket and moveable relative to the first bracket. The second bracket includes a drill plate having a plurality of guide holes defined therein.

17 Claims, 11 Drawing Sheets

(56) References Cited

U.S. PATENT DOCUMENTS

| | | | |
|---|---|---|---|
| 5,129,908 A | 7/1992 | Petersen et al. | |
| 5,147,365 A | 9/1992 | Whitlock et al. | |
| 5,174,693 A * | 12/1992 | Lee et al. | 408/108 |
| 5,222,955 A | 6/1993 | Mikhail et al. | |
| 5,250,050 A | 10/1993 | Poggie et al. | |
| 5,258,032 A | 11/1993 | Bertin | |
| 5,284,482 A * | 2/1994 | Mikhail | 606/86 R |
| 5,284,485 A | 2/1994 | Kammerer et al. | |
| 5,312,409 A | 5/1994 | McLaughlin et al. | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price | |
| 5,520,692 A | 5/1996 | Ferrante et al. | |
| 5,536,271 A | 7/1996 | Daly et al. | |
| 5,542,947 A | 8/1996 | Treacy | |
| D373,635 S | 9/1996 | Price | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,716,361 A | 2/1998 | Masini | |
| 5,716,362 A | 2/1998 | Treacy | |
| 5,827,279 A | 10/1998 | Hughett et al. | |
| 5,941,884 A | 8/1999 | Corvelli et al. | |
| 5,944,723 A | 8/1999 | Colleran et al. | |
| 5,957,926 A | 9/1999 | Masini | |
| 5,968,051 A | 10/1999 | Luckman et al. | |
| 6,010,509 A | 1/2000 | Delgado et al. | |
| 6,056,754 A | 5/2000 | Haines et al. | |
| 6,074,425 A | 6/2000 | Pappas | |
| 6,190,391 B1 | 2/2001 | Stubbs | |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,551,316 B1 | 4/2003 | Rinner et al. | |
| 6,589,248 B1 | 7/2003 | Hughes | |
| 6,851,150 B2 | 2/2005 | Chiang et al. | |
| 6,855,150 B1 | 2/2005 | Linehan | |
| 6,866,667 B2 | 3/2005 | Wood et al. | |
| D549,331 S | 8/2007 | Tomatsu | |
| 7,344,540 B2 | 3/2008 | Smucker et al. | |
| 7,356,902 B2 | 4/2008 | Snider et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn et al. | |
| 2002/0115987 A1 | 8/2002 | Hildwein et al. | |
| 2003/0163137 A1 | 8/2003 | Smucker et al. | |
| 2004/0153066 A1 | 8/2004 | Coon et al. | |
| 2004/0162561 A1 | 8/2004 | Marchyn et al. | |
| 2005/0240196 A1 | 10/2005 | Davis et al. | |
| 2006/0058886 A1 | 3/2006 | Wozencroft | |
| 2006/0142777 A1 | 6/2006 | Bastian et al. | |
| 2007/0118141 A1 * | 5/2007 | Marchyn et al. | 606/88 |
| 2007/0162031 A1 | 7/2007 | Hogg et al. | |
| 2007/0179626 A1 | 8/2007 | de la Barrera et al. | |
| 2007/0233142 A1 | 10/2007 | Oliver | |
| 2007/0260227 A1 | 11/2007 | Phan | |
| 2008/0097450 A1 | 4/2008 | Brown et al. | |
| 2008/0114366 A1 | 5/2008 | Smucker et al. | |
| 2008/0177394 A1 | 7/2008 | Chauhan | |
| 2008/0228190 A1 | 9/2008 | Sherry et al. | |
| 2008/0306484 A1 | 12/2008 | Coon et al. | |
| 2009/0088753 A1 | 4/2009 | Aram et al. | |
| 2009/0264737 A1 | 10/2009 | Haechler et al. | |
| 2009/0326661 A1 | 12/2009 | Wright et al. | |
| 2010/0030223 A1 | 2/2010 | Keller | |
| 2010/0121389 A1 | 5/2010 | Librot et al. | |
| 2010/0152742 A1 | 6/2010 | Nevelös et al. | |
| 2010/0168753 A1 | 7/2010 | Edwards et al. | |
| 2010/0204701 A1 | 8/2010 | Tallarida et al. | |
| 2011/0066193 A1 * | 3/2011 | Lang et al. | 606/86 R |
| 2012/0078261 A1 | 3/2012 | Kecman et al. | |
| 2013/0023883 A1 | 1/2013 | Wright et al. | |
| 2013/0023890 A1 | 1/2013 | Kecman et al. | |
| 2013/0030443 A1 | 1/2013 | Wright et al. | |
| 2013/0030539 A1 | 1/2013 | Wright et al. | |
| 2013/0035693 A1 | 2/2013 | Wright et al. | |
| 2013/0079787 A1 | 3/2013 | Jones et al. | |
| 2013/0079788 A1 | 3/2013 | Jones et al. | |
| 2013/0079789 A1 | 3/2013 | Randle et al. | |
| 2013/0211410 A1 | 8/2013 | Landes et al. | |

FOREIGN PATENT DOCUMENTS

| | | |
|---|---|---|
| EP | 1723916 B1 | 11/2006 |
| EP | 1967143 A2 | 9/2008 |
| EP | 2574314 A1 | 4/2013 |
| FR | 2737848 A1 | 2/1997 |
| GB | 2433698 A | 7/2007 |
| WO | 9945856 A1 | 9/1999 |
| WO | 2005110249 A1 | 11/2005 |
| WO | 2008112996 A1 | 9/2008 |

OTHER PUBLICATIONS

Depuy Orthopaedics, Inc., LCS High Performance Instruments, Surgical Technique Guide, 2008, (44 Pages), Pub. No. 0612-85-506, Depuy Orthopaedics, Inc., Warsaw, IN.

Depuy Orthopaedics, Inc. Sigma High Performance Instruments, Classic Surgical Technique, 2010, (52 Pages), Pub. No. 0612-89-510, Depuy Orthopaedics, Inc., Warsaw, IN.

Depuy Orthopaedics, Inc., Sigma High Performance Instruments, Design Rationale, 2007 (12 Pages), Pub. No. 0612-54-506 (Rev. 2), Depuy Orthopaedics, Inc., Warsaw, IN.

European Search Report, European Pat. App. No. 11175824.9-2310, Dec. 16, 2011 (7 Pages).

European Search Report, European Pat. App. No. 12191753.8-2310, Jan. 3, 2013 (6 Pages).

European Search Report for European Application No. 12174683.8-2310, Sep. 3, 2012, 6 pages.

European Search Report for European Application No. 12174682.0-2310, Sep. 5, 2012, 6 pages.

International Search Report, International Application No. PCT/US12/44947, Oct. 12, 2012, 3 pages.

European Search Report for European Application No. 12186675.0-2310, Dec. 12, 2012, 7 pages.

European Search Report for European Application No. 12186700.6-2310, Dec. 13, 2012, 8 pages.

European Search Report for European Application No. 12186728.7-2310, Dec. 14, 2012, 8 pages.

* cited by examiner

PATELLA CLAMP AND DRILL GUIDE SURGICAL INSTRUMENT

This application claims priority under 35 U.S.C. §119 to U.S. Provisional Application Ser. No. 61/503,419 entitled "PATELLA CLAMP AND DRILL GUIDE SURGICAL INSTRUMENT," which was filed on Jun. 30, 2011, the entirety of each of which is incorporated herein by reference.

CROSS-REFERENCES TO RELATED U.S. PATENT APPLICATIONS

Cross-reference is made to U.S. Provisional Patent Application Ser. No. 61/503,164 entitled "PATELLA DRILL GUIDE AND CLAMP ASSEMBLY" by Abraham Wright et al., and co-pending U.S. Design patent application Ser. No. 29/396,511 entitled "PATELLA DRILL GUIDE AND CLAMP" by Abraham Wright et al., each of which is assigned to the same assignee as the present application, is filed concurrently herewith, and is hereby incorporated by reference.

TECHNICAL FIELD

The present disclosure relates generally to orthopaedic surgical instruments and, more particularly, to patella surgical instruments.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To secure the prosthetic component to the patella, an orthopaedic surgeon may resect the posterior side of the patient's natural patella to prepare the natural patella to receive the prosthetic component. In use, the patella prosthetic component articulates with the patient's natural or prosthetic femur during extension and flexion of the patient's knee.

To facilitate the replacement of the natural joint with the knee prosthesis, orthopaedic surgeons use a variety of orthopaedic surgical instruments such as, for example, cutting blocks, drill guides, milling guides, and other surgical instruments.

SUMMARY

According to one aspect of the disclosure, an orthopaedic surgical instrument is disclosed. The orthopaedic surgical instrument includes a patella drill guide that has a first bracket and a second bracket moveably coupled to the first bracket, and a gasket that is removably coupled to the second bracket. The second bracket includes a drill plate having a plurality of guide holes defined therein, and the drill plate is formed from a substantially transparent material. Each of the plurality of guide holes is sized to receive a surgical drill. The gasket is configured to cover the guide holes when coupled to the second bracket.

In some embodiments, the first bracket may include a mounting plate. The mounting plate may have a first clamping surface with a first plurality of teeth extending therefrom. The drill plate of the second bracket may include a first clamping surface facing the first clamping surface of the mounting plate. The first clamping surface of the drill plate may have a second plurality of teeth extending therefrom.

In some embodiments, the first clamping surface of the mounting plate may extend substantially parallel to the first clamping surface of the drill plate. Additionally, in some embodiments, the gasket may have a first surface configured to contact the first clamping surface of the drill plate. The first surface of the gasket may have a plurality of positioning holes defined therein that are configured to receive the second plurality of teeth of the drill plate. In some embodiments, the gasket may have a concave second surface opposite the first surface.

In some embodiments, the first clamping surface of the drill plate may have a plurality of etch marks defined therein. Each etch mark may correspond to a size of a patient's patella. Additionally, in some embodiments, the plurality of etch marks may be arranged as a plurality of inscribed lines defined in the first clamping surface of the drill plate. In some embodiments, the drill plate may have a front surface positioned opposite the first clamping surface. Each inscribed line may be visible through the front surface.

In some embodiments, the mounting plate and the drill plate may be formed from a polymeric material. In some embodiments, the orthopaedic surgical instrument may include a plurality of metal bushings attached to the drill plate. Each metal bushing may define a corresponding one of the plurality of guide holes.

Additionally, in some embodiments, the plurality of guide holes of the drill plate may be arranged in a triangular pattern. In some embodiments, the gasket may be formed from an elastomeric material.

According to another aspect of the disclosure, an orthopaedic surgical instrument has a housing including a handle and a first bracket. The first bracket has a mounting plate and a plurality of teeth extending therefrom. The orthopaedic surgical instrument also includes a second bracket moveably coupled to the housing. The second bracket has a drill plate spaced apart from the mounting plate of the first bracket, and the drill plate includes a plurality of guide holes. Each of the guide holes is sized to receive a surgical drill, and a plurality of teeth extend from the drill plate toward the mounting plate. The orthopaedic surgical instrument further includes a clamp actuation mechanism coupled to the housing and the second bracket. The clamp actuation mechanism is operable to move the second bracket in a first direction toward the first bracket.

In some embodiments, each of the plurality of guide holes may have a longitudinal axis extending therethrough. The second bracket may include a beam moveably coupled to the housing. The beam may be configured to move relative to the housing along an axis extending parallel to the longitudinal axes of the guide holes. Additionally, in some embodiments, the clamp actuation mechanism may include an actuation plate positioned in the housing and configured to engage the beam. The actuation plate may include a follower surface. The clamp actuation mechanism may include a lever pivotally coupled to the housing such that the lever is moveable between a first position and a second position. The lever may include a cam surface configured to engage the follower surface of the actuation plate when the lever is moved from the first position to the second position such that the actuation plate engages the beam to move the second bracket along the axis in the first direction.

In some embodiments, the clamp actuation mechanism may include a biasing element positioned between the actuation plate and an inner wall of the housing.

Additionally, in some embodiments, the orthopaedic surgical instrument may further include a locking mechanism configured to selectively prevent movement of the second bracket in a second direction away from the first bracket. In some embodiments, the locking mechanism may include a locking plate moveable between a first position in which the locking plate engages the beam to prevent movement of the second bracket in the second direction, and a second position in which the locking plate is disengaged from the beam such that the second bracket is permitted to move in the second direction. The locking mechanism may include a biasing element positioned between the locking plate and the housing. The biasing element may be configured to bias the locking plate in the first position. In some embodiments, the orthopaedic surgical instrument may include a release button attached to the locking plate.

According to another aspect, the orthopaedic surgical instrument includes a polymeric housing including a handle and a first bracket. The first bracket may have a mounting plate and a plurality of teeth extending therefrom. The orthopaedic surgical instrument also includes a second bracket moveably coupled to the housing. The second bracket has a drill plate formed from a substantially transparent material. The drill plate includes a clamping surface, a front surface, and a plurality of guide holes extending through the clamping surface and the front surface. Each of the guide holes is sized to receive a surgical drill. A plurality of etch marks are defined in the clamping surface of the drill plate. The plurality of etch marks are visible through the front surface. The orthopaedic surgical instrument further includes a clamp actuation mechanism coupled to the polymeric housing and the second bracket and a locking mechanism coupled to the housing and the second bracket. The clamp actuation mechanism is operable to move the second bracket in a first direction toward the first bracket, and the locking mechanism is configured to selectively prevent movement of the second bracket in a second direction away from the first bracket.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
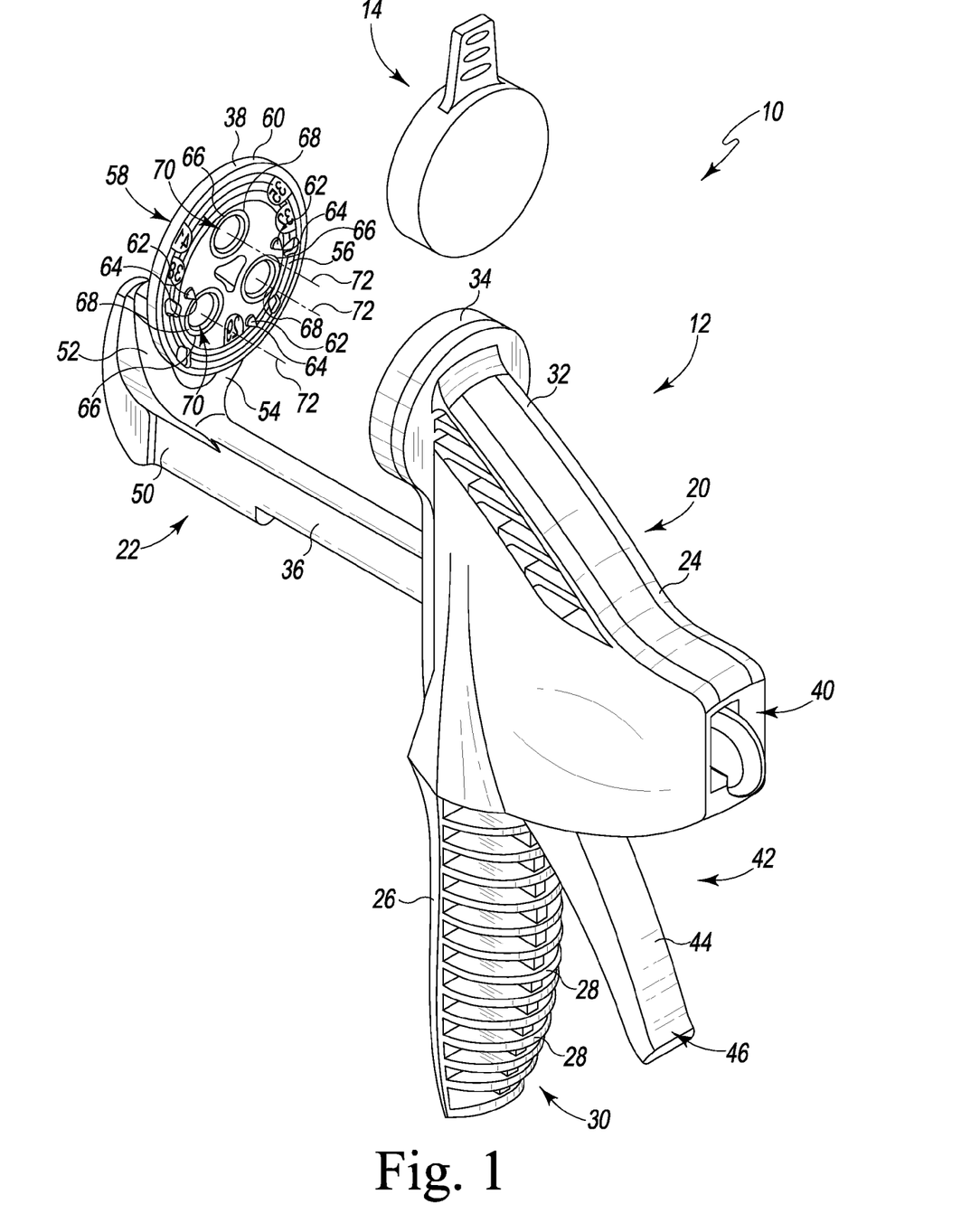
FIG. 1 is a perspective view of an orthopaedic surgical instrument.

Referring to FIG. 1, an orthopaedic surgical instrument 10 includes a patella clamp and drill guide 12 (hereinafter guide 12) and a compression gasket 14 configured to be secured to the guide 12. As described in greater detail below, the instrument 10 is utilized to surgically prepare a patient's resected patella 16 (see FIG. 9) for implantation of a patella prosthetic component, such as a patella prosthetic component 18 (see FIG. 9). To do so, the patient's resected patella 16 may be positioned in the guide 12, and the surgeon may use the guide 12 to drill fixation holes into the planar, resected posterior surface. The surgeon may also use the guide 12 to size and select a patella prosthetic component suitable for use with the particular patient's patella. After the patella prosthetic component is selected, the surgeon may use the guide 12 and the gasket 14 to secure the selected patella prosthetic component to the patient's resected patella.

As shown in FIG. 1, the guide 12 of the instrument 10 includes a housing 20 and a clamping bracket 22 configured to move relative to the housing 20. The housing 20 has a main body 24 and a handle 26 extending downwardly from the main body 24. The handle 26 includes a plurality of ribs 28 that define a grip 30, which is sized to be grasped by a hand of a surgeon. The housing 20 also includes a support bracket 32 that extends from the main body 24 opposite the handle 26. The support bracket 32 has a mounting plate 34 configured to engage the anterior side of the patient's resected patella 16.

The clamping bracket 22 of the guide 12 includes a beam 36 and a drill plate 38 attached to the beam 36. The beam 36 is received in a passageway 40 defined in the main body 24 of the housing 20 and is configured to slide relative to the housing 20. The guide 12 also has a clamp actuation mechanism 42 that includes a lever or trigger arm 44 extending downwardly from the main body 24 of the housing 20. The trigger arm 44 is configured to pivot relative to the housing 20 when force is applied as indicated by arrow 46. By operating the trigger arm 44, the drill plate 38 of the clamping bracket 22 may be advanced toward the mounting plate 34 of the support bracket 32, as described in greater detail below.

The beam 36 of the clamping bracket 22 extends outwardly from the passageway 40 of the housing 20 to an end 50. A pair of mounting arms 52, 54 extends upwardly from the end 50 of the beam 36, and the drill plate 38 is secured to the mounting arms 52, 54. In the illustrative embodiment, the drill plate 38 and the beam 36 are formed separately and later assembled. It should be appreciated that in other embodiments the beam 36 and the drill plate 38 may be molded or otherwise formed as a single monolithic component.

The drill plate 38 of the clamping bracket 22 has a planar clamping surface 56 that faces the mounting plate 34, a front surface 58 opposite the clamping surface 56, and a side wall 60 that connects the surfaces 56, 58. A plurality of teeth 62 extend from the clamping surface 56 toward the mounting plate 34 of the support bracket 32, and each tooth 62 includes a tip 64 configured to engage the patient's resected patella 16. As shown in FIG. 1, the drill plate 38 includes three teeth 62 that are arranged in a triangular pattern on the clamping surface 56. It should be appreciated that in other embodiments the drill plate 38 may include additional teeth or fewer teeth arranged in other geometric patterns. Additionally, in other embodiments, the teeth may be removably attached to the drill plate 38.

The drill plate 38 also includes a plurality of cylindrical openings 66 extending through the surfaces 56, 58. The openings 66 are arranged in a triangular pattern, and each opening 66 has a bushing 68 positioned therein. A guide hole 70 of the drill plate 38 is defined through each bushing 68, and each guide hole 70 has a longitudinal axis 72 extending therethrough. As described in greater detail below, each guide hole 70 is sized to receive a surgical drill 74 (see FIG. 11) and guide the drill 74 along the axis 72 into contact with the patient's resected patella 16. In the illustrative embodiment, the drill plate 38 has three guide holes 70. It should be appreciated that in other embodiments the drill plate 38 may include additional or fewer guide holes 70 arranged in a geometric patterns other than the triangular pattern shown in FIG. 1.

The bushings 68 of the drill plate 38 are formed from a metallic material such as stainless steel. In other embodiments, the bushings 68 may be formed from a polymeric material resistant to wear. It should also be appreciated that in other embodiments the bushings 68 may be omitted.

The housing 20 and the beam 36 of the clamping bracket 22 are each formed from a polymeric material, such as, for example, polyethylene. In other embodiments, the housing 20 and the beam 36 may be formed from a metallic material such as stainless steel. The drill plate 38 is formed from a substantially transparent material. In the illustrative embodiment, the drill plate 38 is formed from an acrylate polymer, such as, for example, polycarbonate. It should also be appreciated that the drill plate 38 may be formed from other substantially transparent material, such as, for example, methyl acrylate or glass.

Figure 2:
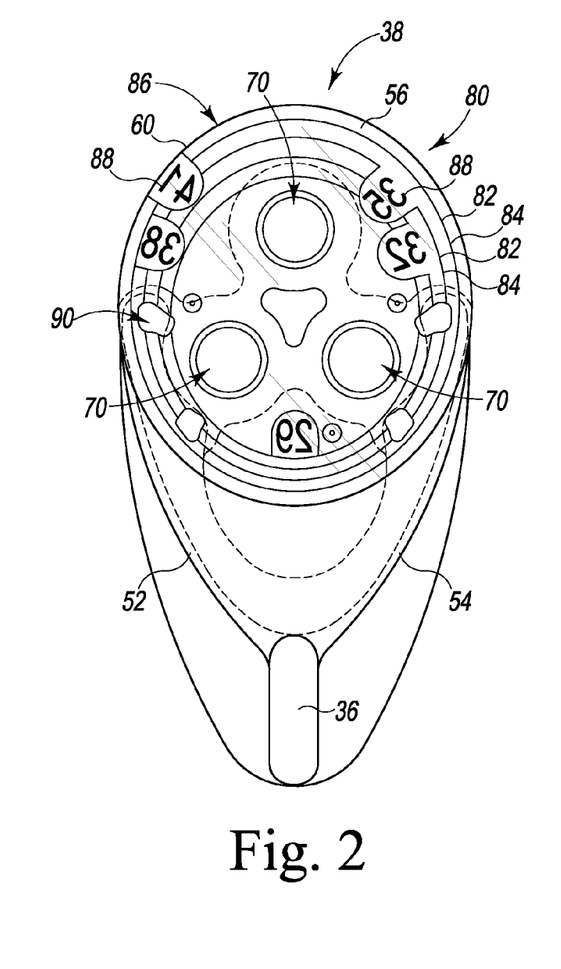
FIG. 2 is a rear elevation view of a drill plate of the orthopaedic surgical instrument of FIG. 1.
Figure 3:
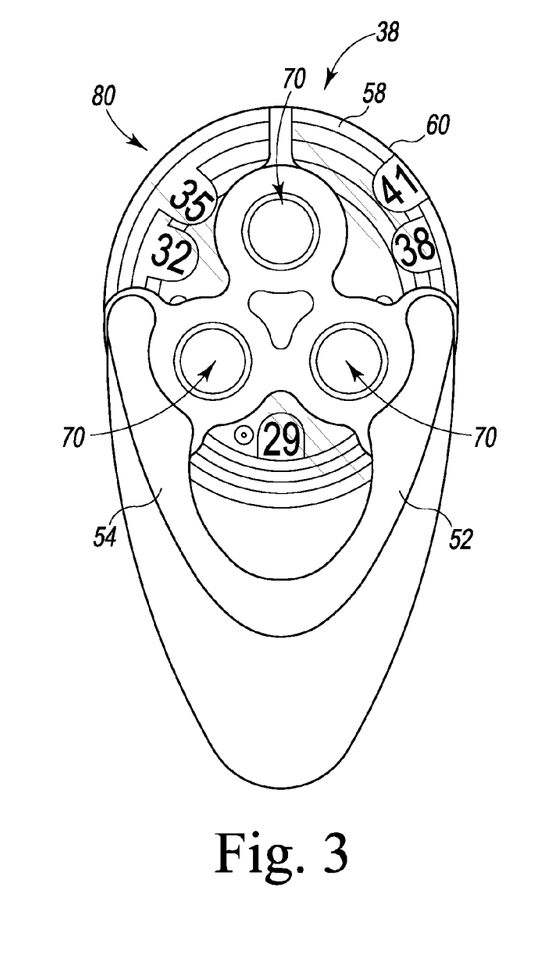
FIG. 3 is a front elevation view of the drill plate of FIG. 2.

Referring now to FIGS. 2 and 3, the drill plate 38 of the clamping bracket 22 includes multiple indicators 80 that correspond to multiple sizes of the patient's patella. The indicators 80 include a plurality of etch marks 82 that are defined in the clamping surface 56, each of which corresponds to a different size of a patient's patella. As shown in FIG. 2, the etch marks 82 are arranged as a number of inscribed lines 84 that indicate narrow and intermediate sizes. The indicators 80 also include an outer circumference 86 of the side wall 60 of the drill plate 38, which indicates the widest patella size of the patella sizes indicated by the indicators 80. In other embodiments, the drill plate 38 may be larger and include additional indicators 80 corresponding to other possible sizes of the patient's patella.

Each of the indicators 80 is identified by a corresponding numerical symbol 88, which, in turn, corresponds to a particular patella size. When the indicators 80 are viewed as shown in FIG. 2, the numerical symbols 88 appear backward or mirrored. When viewed as shown in FIG. 3, the etch marks 82 and the numerical symbols 88 are properly oriented and visible through the front surface 58 because the drill plate 38 is substantially transparent. Similarly, when a patient's resected patella is positioned between the drill plate 38 and the mounting plate 34, the patella is also visible through the front surface 58. It should be appreciated that in other embodiments the lines and indicators may be formed on the plate 38 via printing or painting rather than by etching.

Referring now to FIGS. 4-7, the clamp actuation mechanism 42 of the guide 12 is shown in greater detail. As described above, the clamp actuation mechanism 42 includes a trigger arm 44 that extends downwardly from the main body 24 of the housing 20, and the trigger arm 44 may be operated to move the clamping bracket 22 relative to the housing 20 in the direction indicated by arrow 98. The trigger arm 44 has a body 100 including a lower lever arm 102 positioned below the main body 24 adjacent to the handle 26. The body 100 also includes an upper lever arm 104 that is positioned within the main body 24 of the housing 20.

Figure 4:
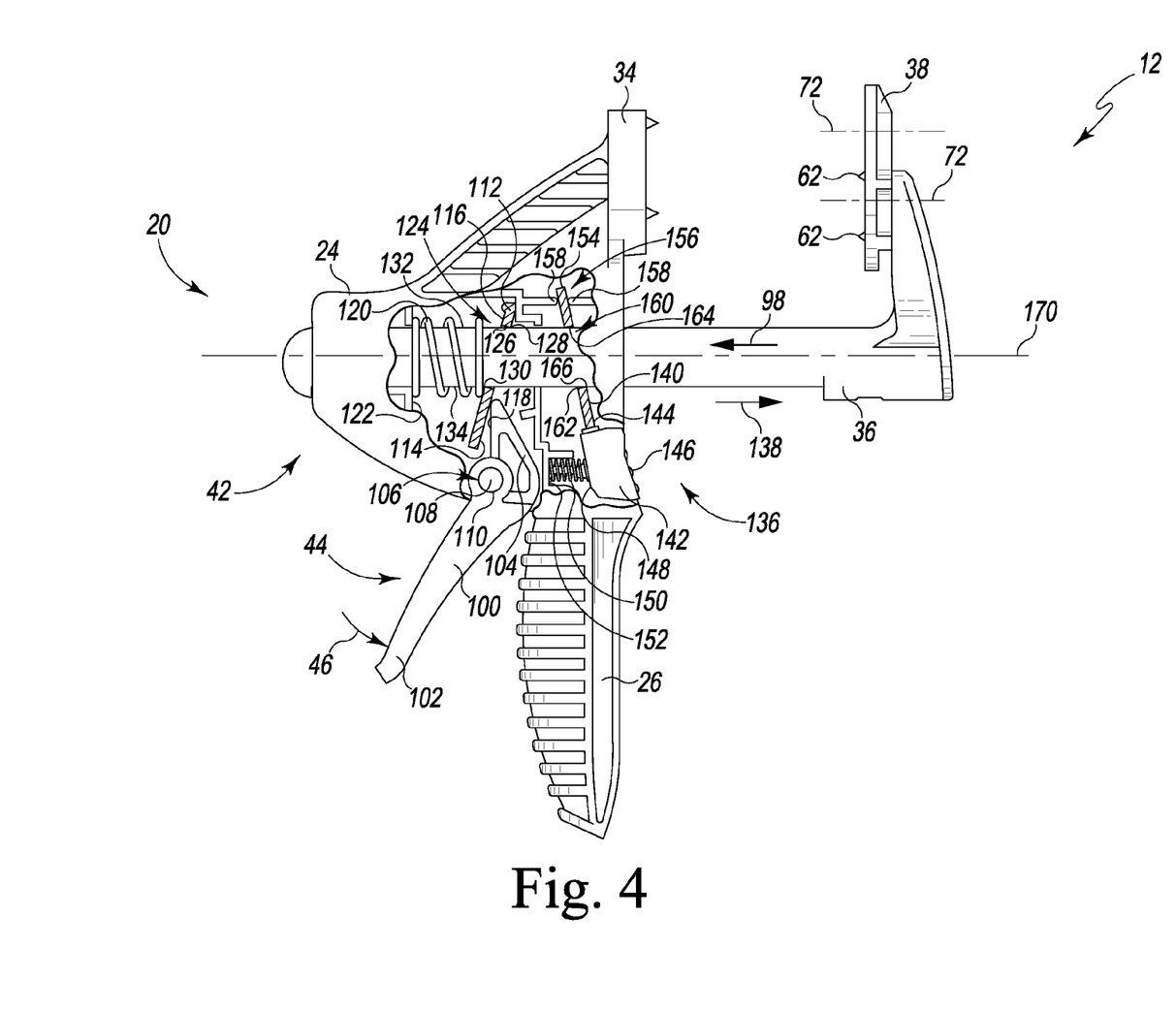
FIG. 4 is a partial cutaway side elevation view of the orthopaedic surgical instrument of FIG. 1 showing the drill plate in one position relative to a housing of the orthopaedic surgical instrument.

As shown in FIG. 4, the body 100 of the trigger arm 44 is attached to the main body 24 via a joint 106. The joint 106 includes a cylindrical pin 108 positioned in a cylindrical opening 110 defined through the body 100 and a pair of mounting holes (not shown) defined in the main body 24 of the housing 20. In that way, the trigger arm 44 is configured to pivot relative to the housing 20 between the extended position shown in FIG. 4 and the compressed position shown in FIG. 5.

The clamp actuation mechanism 42 also includes an actuation plate 112 that has a front surface 114 and a rear surface 116. As shown in FIGS. 4-7, the upper lever arm 104 of the trigger arm 44 includes a cam surface 118 that engages the front surface 114 of the actuation plate 112. The clamp actuation mechanism 42 also includes a biasing element, such as, for example, a spring 120, which extends over the beam 36 of the clamping bracket 22 and is positioned between rear surface 116 of the actuation plate 112 and an inner wall 122 of the housing 20. The spring 120 is configured to bias the clamp actuation mechanism 42 in the extended position shown in FIG. 4.

The actuation plate 112 of the clamp actuation mechanism 42 has a closed slot 124 extending through the surfaces 114, 116 of the plate 112. As shown in FIG. 4, the actuation plate 112 is positioned over the beam 36, and the beam 36 extends through the slot 124. The slot 124 is defined by an inner wall 126 that extends between the surfaces 114, 116. The inner wall 126 of the actuation plate 112 includes a pair of engagement edges 128, 130 that grip an upper surface 132 and a lower surface 134, respectively, of the beam 36.

The guide 12 of the instrument 10 also includes a locking mechanism 136 that inhibits movement of the clamping bracket 22 relative to the housing 20, including selectively preventing movement of the bracket 22 in the direction indicated by arrow 138. The locking mechanism 136 includes a locking plate 140 positioned in the main body 24 of the housing 20 and a release button 142 attached to a lower end 144 of the locking plate 140. The release button 142 includes a contoured front surface 146 and a rear surface 148 opposite the front surface 146. The locking mechanism 136 also includes a biasing element, such as, for example, a spring 150 that is positioned between the rear surface 148 of the button 142 and an inner wall 152 of the housing 20.

An upper end 154 of the locking plate 140 is positioned in a slot 156 defined between a pair of flanges 158 of the housing 20. The locking plate 140, like the actuation plate 112, has a closed slot 160 extending therethrough. As shown in FIG. 4, the locking plate 140 is positioned over the beam 36, and the beam 36 extends through the slot 160. The slot 160 is defined by an inner wall 162 having a pair of engagement edges 164, 166 that grip the upper surface 132 and the lower surface 134, respectively, of the beam 36 to inhibit movement of the clamping bracket 22 relative to the housing 20.

In use, the surgeon may utilize the clamp actuation mechanism 42 to advance the drill plate 38 of the clamping bracket 22 toward the mounting plate 34 of the support bracket 32. To do so, the surgeon or other user exerts a force on the lower lever arm 102 of the trigger arm 44 in the direction indicated by arrow 46. The force is transferred from the trigger arm 44 to the actuation plate 112 through the engagement of the cam surface 118 of the upper lever arm 104 with the front surface 114 of the actuation plate 112. As force is applied to the lower lever arm 102, the engagement edges 128, 130 of the actuation plate 112 grip the upper surface 132 and the lower surface 134, respectively, of the beam 36, and the actuation plate 112 pushes against the spring 120. When a predetermined amount of force is applied to the trigger arm 44, the actuation plate 112 overcomes the bias of the spring 120 and the drill plate 38 advances toward the mounting plate 34 in the direction indicated by arrow 98.

Figure 5:
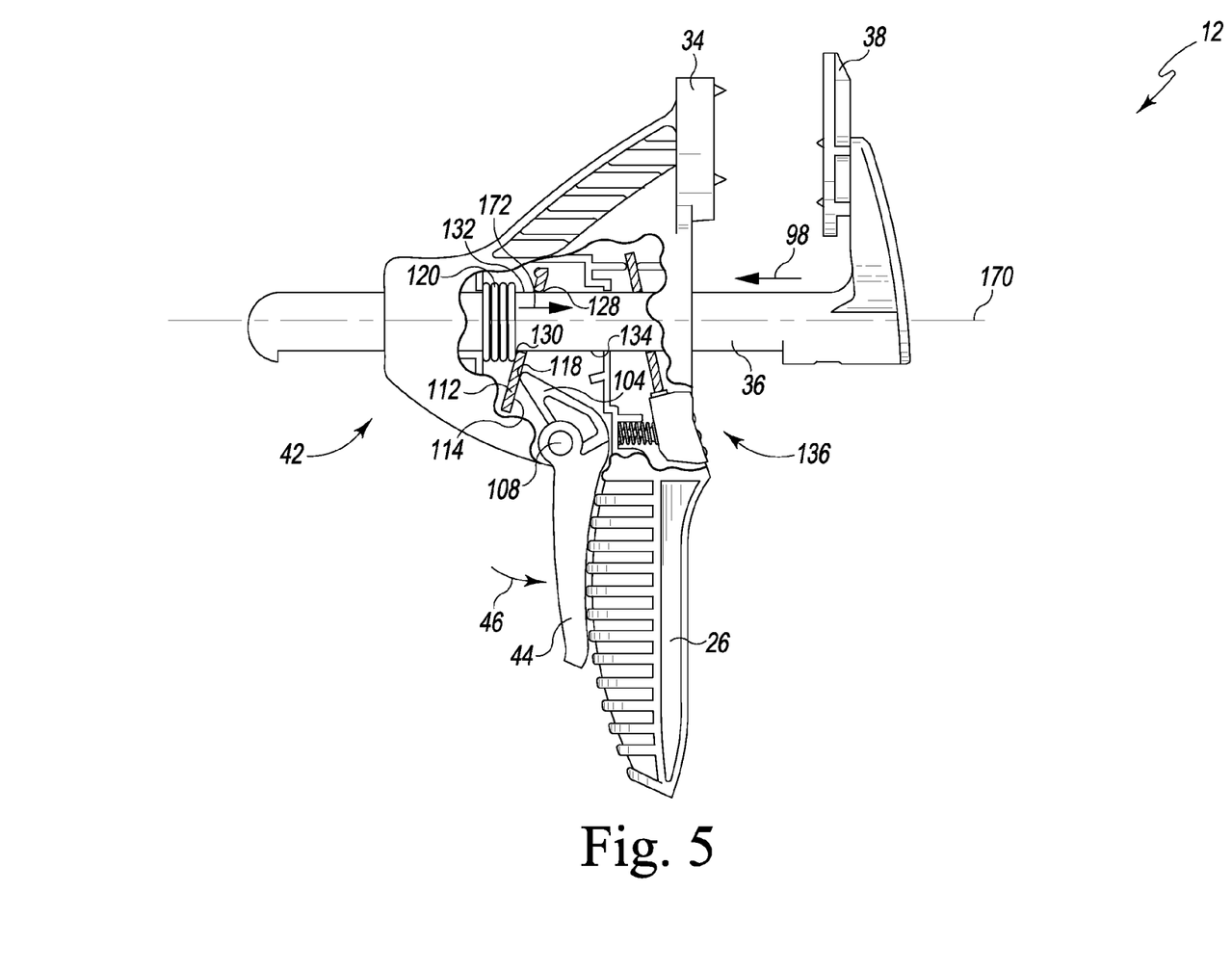
FIG. 5 is a partial cutaway side elevation view of the orthopaedic surgical instrument of FIG. 1 showing the drill plate in another position relative to the housing.

As shown in FIGS. 4 and 5, the upper lever arm 104 of the trigger arm 44 moves downward along the front surface 114 of the actuation plate 112 as the trigger arm 44 pivots relative to the housing 20. The beam 36 of the clamping bracket 22 is drawn by the actuation plate 112 through the passageway 40, moving along an axis 170 that extends parallel to the longitudinal axes 72 defined by the guide holes 70 of the drill plate 38. The movement of the clamping bracket 22 relative to the housing 20 continues until the lower lever arm 102 of the trigger arm 44 contacts the handle 26 in the compressed position shown in FIG. 5.

When the user releases the trigger arm 44, the removal of the force exerted by the upper lever arm 104 causes the engagement edges 128, 130 of the actuation plate 112 to disengage from the surface 132, 134, respectively, of the beam 36. The spring 120 urges the actuation plate 112 to move in the direction indicated by arrow 172 while the clamping bracket 22 is held in position relative to the housing 20 by the locking mechanism 136. The force exerted by the spring 120 is transferred from the actuation plate 112 to the trigger arm 44 through the engagement of the front surface 114 of the actuation plate 112 with the cam surface 118 of the upper lever arm 104. The trigger arm 44 is thereby urged to pivot relative to the housing 20 in the direction indicated by arrow 174 and return to the extended position shown in FIG. 6.

Figure 6:
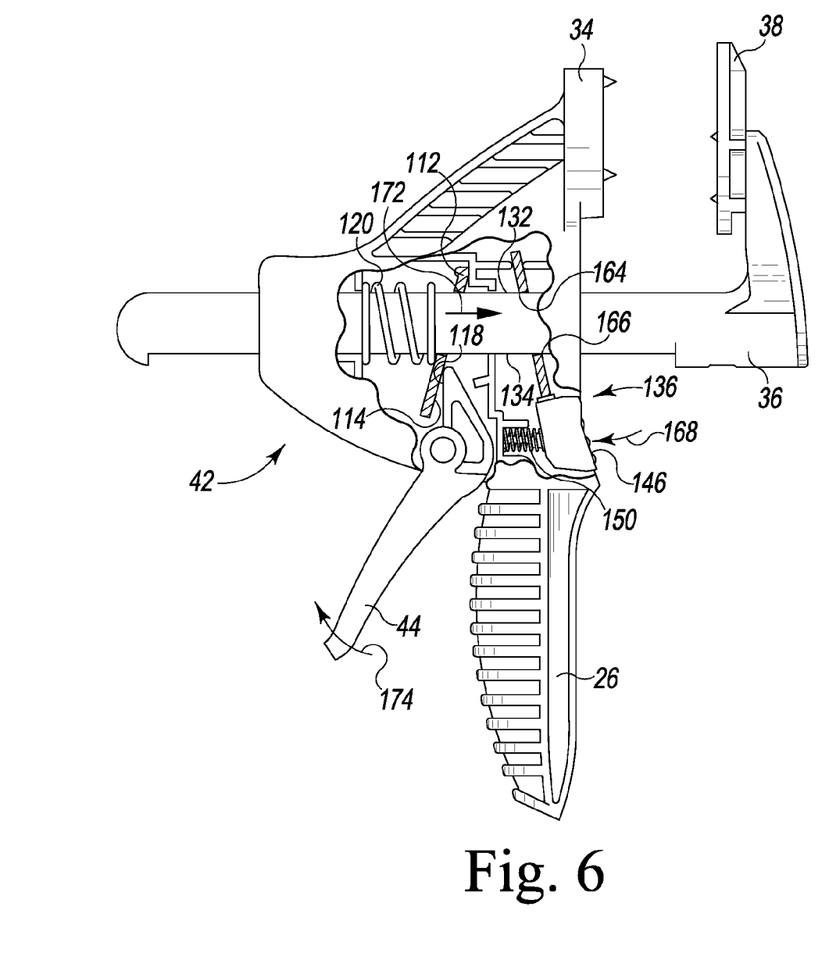
FIG. 6 is a partial cutaway side elevation view similar to FIG. 5.

In the extended position, the trigger arm 44 is prevented from pivoting further relative to the housing 20, and the actuation plate 112 is locked in position between the spring 120 and the upper lever arm 104. In that position, the engagement edges 128, 130 of the actuation plate 112 grip the upper surface 132 and the lower surface 134, respectively, of the beam 36. The surgeon or user may repeat the steps outlined above to advance the drill plate 38 closer to the mounting plate 34.

Figure 7:
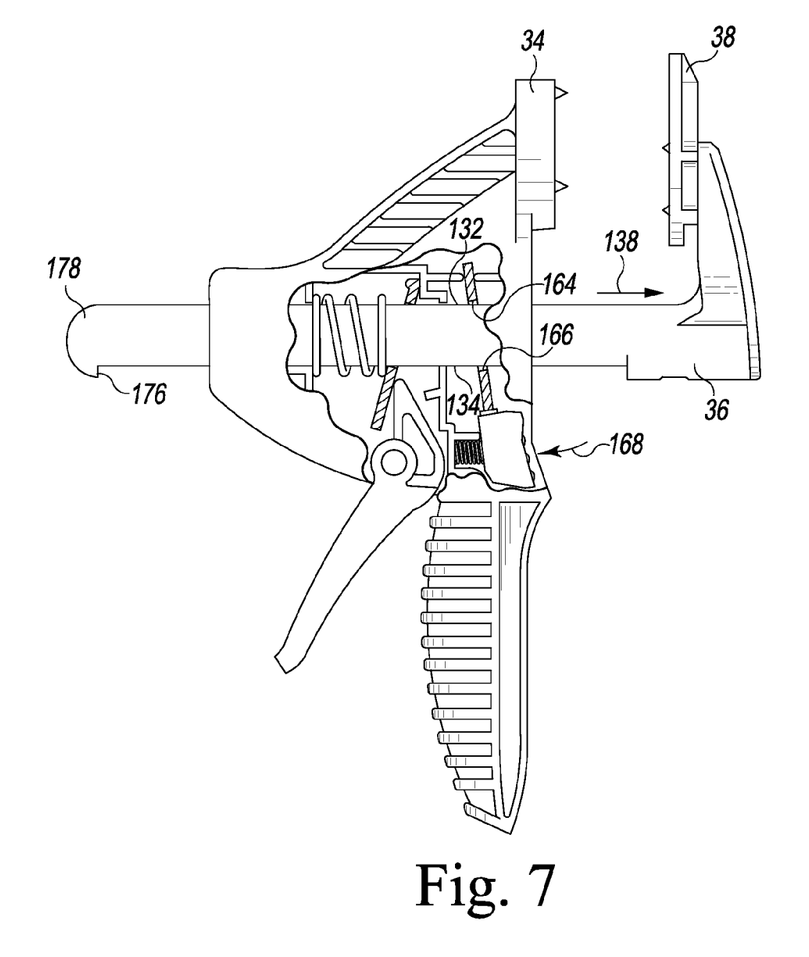
FIG. 7 is a partial cutaway side elevation view similar to FIGS. 5 and 6.

When the surgeon or other user desires to move the drill plate 38 away from the mounting plate 34, the surgeon may actuate the release button 142 to release the locking mechanism 136, thereby permitting the clamping bracket 22 to move in the direction indicated by arrow 138, as shown in FIGS. 6 and 7. To do so, a predetermined amount of force is applied to the contoured front surface 146 of the button 142 in the direction indicated by arrow 168 to overcome the bias exerted by spring 150. When a sufficient amount of force is applied, the locking plate 140 tilts such that the engagement edges 164, 166 of the locking plate 140 are released from the surfaces 132, 134 of the beam 36, as shown in FIG. 7. The clamping bracket 22 may then be manually moved along the axis 170 in the direction indicated by arrow 138 to any position relative to the housing 20. The user is prevented from detaching the clamping bracket 22 from the housing 20 by a stop 176 defined on an end 178 of the beam 36. When the clamping bracket 22 is located at the desired position, the button 142 may be released to re-engage the edges 164, 166 of the locking plate 140 with the surfaces 132, 134 of the beam 36 and thereby prevent further movement of the clamping bracket 22 relative to the housing 20.

Figure 8:
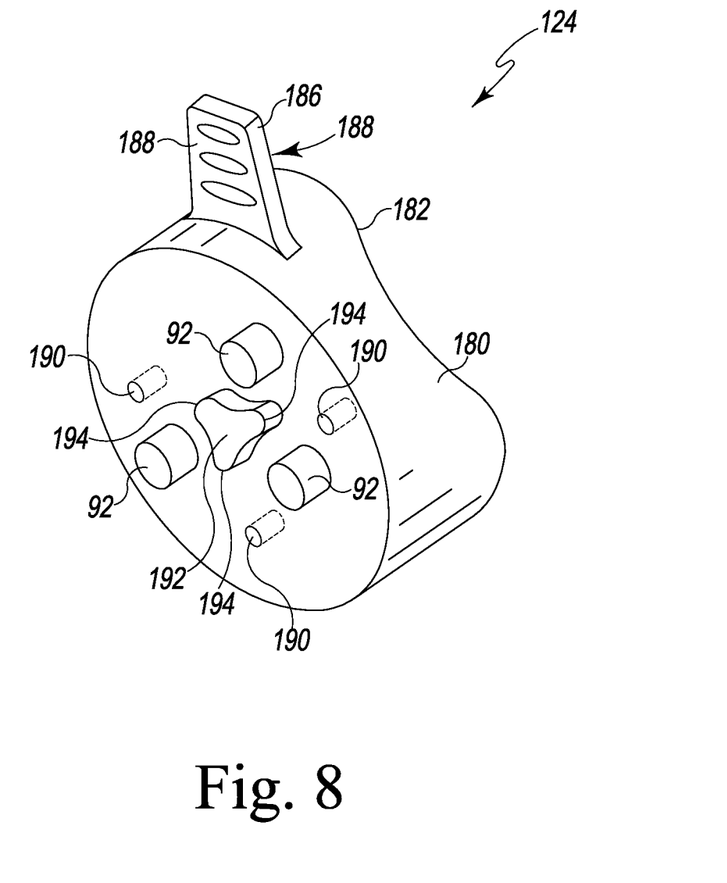
FIG. 8 is a perspective view of a compression gasket of the orthopaedic surgical instrument of FIG. 1.

Referring now to FIG. 8, the compression gasket 14 is shown in greater detail. The gasket 14 has a body 180 formed from an elastomeric material such as rubber. It should be appreciated that in other embodiments the body 180 may be formed from a polymeric material. The body 180 has a side surface 182 that is concave and is configured to receive a portion of the patella prosthetic component 18, as will be described in greater detail below.

The body 180 of the gasket 14 has another side surface 184 opposite the side surface 182. A plurality of mounting plugs 92 extend from the side surface 184. Each mounting plug 92 is sized to be received in a corresponding guide hole 70 of the drill plate 38. The body 180 also has a plurality of holes 190 defined in the side surface 184 that are sized to receive each of the teeth 62 extending from the clamping surface 56 of the drill plate 38.

A tab 186 extends outwardly from the body 180 of the gasket 14. The tab 186 includes a pair of contoured surfaces 188 configured to receive the fingertips of the user. In use, the user may grip the surfaces 188 to move the gasket 14 relative to the drill plate 38, thereby moving the gasket 14 out of the drilling path when preparing to drill holes in a patient's resected patella. In that way, the plugs 92 of the gasket 14 may be moved into and out of the guide holes 70 of the drill plate 38.

The mounting plugs 92 include a central plug 192 having a configuration that substantially corresponds to the configuration of the central aperture 94 of the drill plate 38. In particular, the central plug 192 includes a trio of arms 194 that are sized and arranged to fit in the corresponding trio of extension slots 96 of the aperture 94 such that the gasket 14 is attached to the drill plate 38 in a predetermined orientation.

Figure 9:
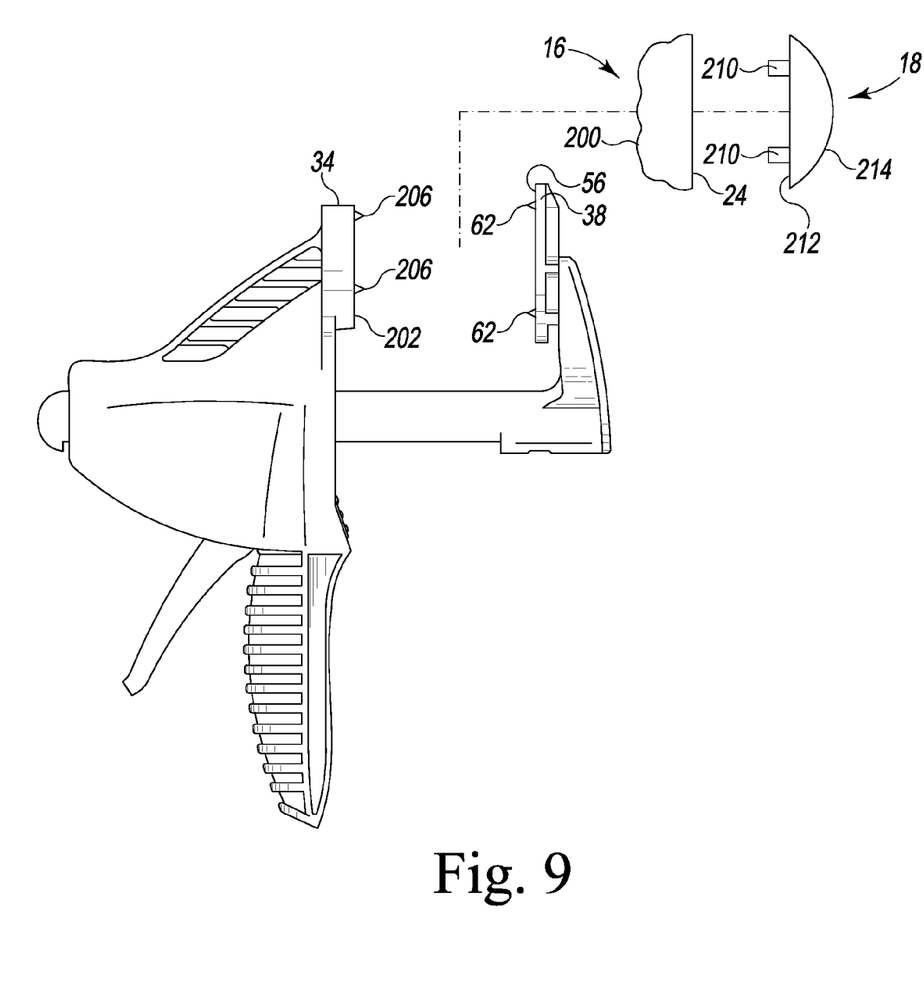
FIG. 9 is a side elevation view of the orthopaedic surgical instrument of FIG. 1 with a patient's resected patella and a prosthetic patella component.

As described above, the guide 12 may be utilized to surgically prepare a patient's resected patella 16 for implantation of a patella prosthetic component 18, as shown in FIGS. 9-12. To do so, the surgeon may position the resected patella 16 between the mounting plate 34 and the drill plate 38 of the guide 12 with the compression gasket 14 decoupled from the guide 12. As shown in FIG. 9, the patient's resected patella 16 may be positioned between the plates 34, 38 such that an anterior surface 200 of the resected patella 16 faces a planar clamping surface 202 of the mounting plate 34 and a resected posterior surface 204 of the resected patella 16 faces the planar clamping surface 56 of the drill plate 38.

The planar clamping surface 202 of the mounting plate 34 extends parallel to the planar clamping surface 56 of the drill plate 38 and includes a plurality of teeth 206 extending therefrom. When the patient's resected patella 16 is positioned between the plates 34, 38, the surgeon may move the anterior surface 200 of the patient's resected patella 16 into contact with the plurality of teeth 206 of the planar clamping surface 202. The surgeon may also clamp the patient's resected patella 16 between the plates 34, 38 by operating the clamp actuation mechanism 42 as described above to advance the drill plate 38 toward the mounting plate 34.

Figure 10:
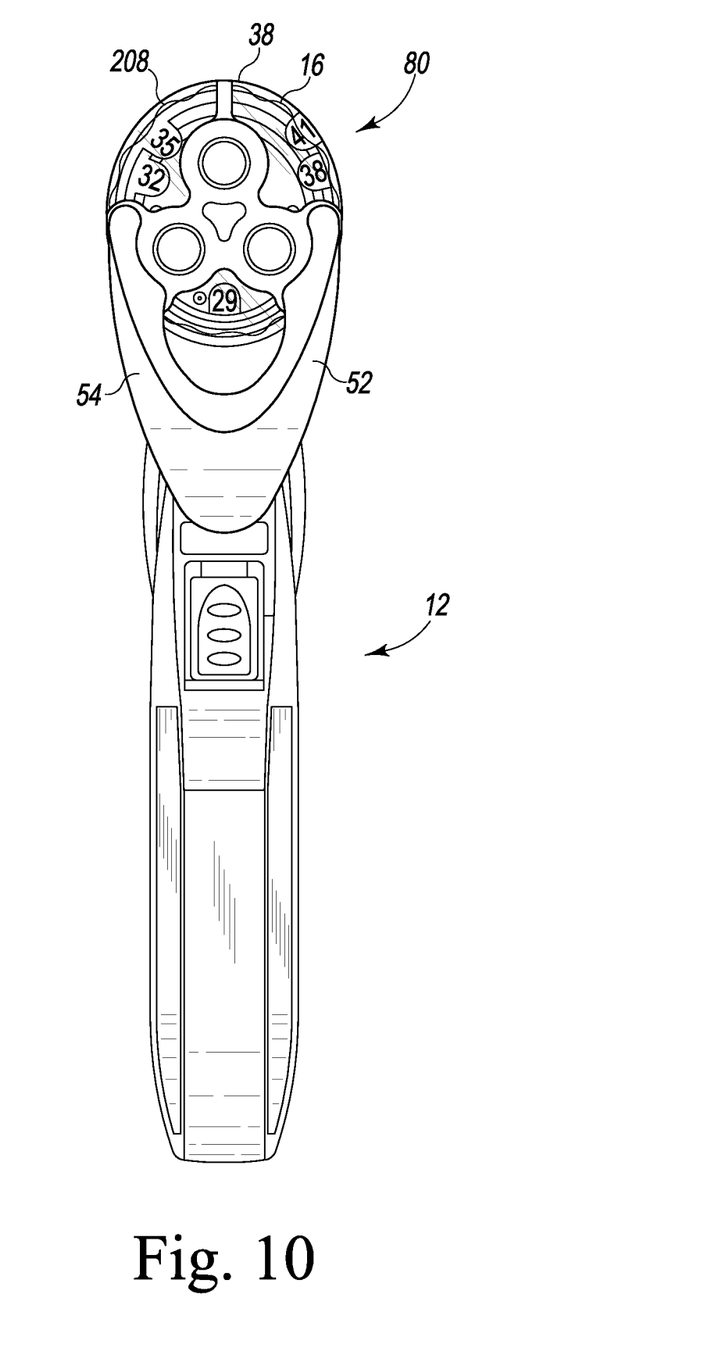
FIG. 10 is a front elevation view of the orthopaedic surgical instrument of FIG. 1 with the patient's resected patella positioned between the drill plate and a mounting plate of the orthopaedic surgical instrument.

Additionally, the surgeon may use the guide 12 to select a patella prosthetic component. As shown in FIG. 10, the outer margin 208 of the patient's resected patella 16 falls within one of the indicators 80, which corresponds to a particular size. Using the indicators 80, the surgeon may select a patella prosthetic component that offers the maximum coverage of the resected posterior surface 204 of the resected patella 16.

Figure 11:
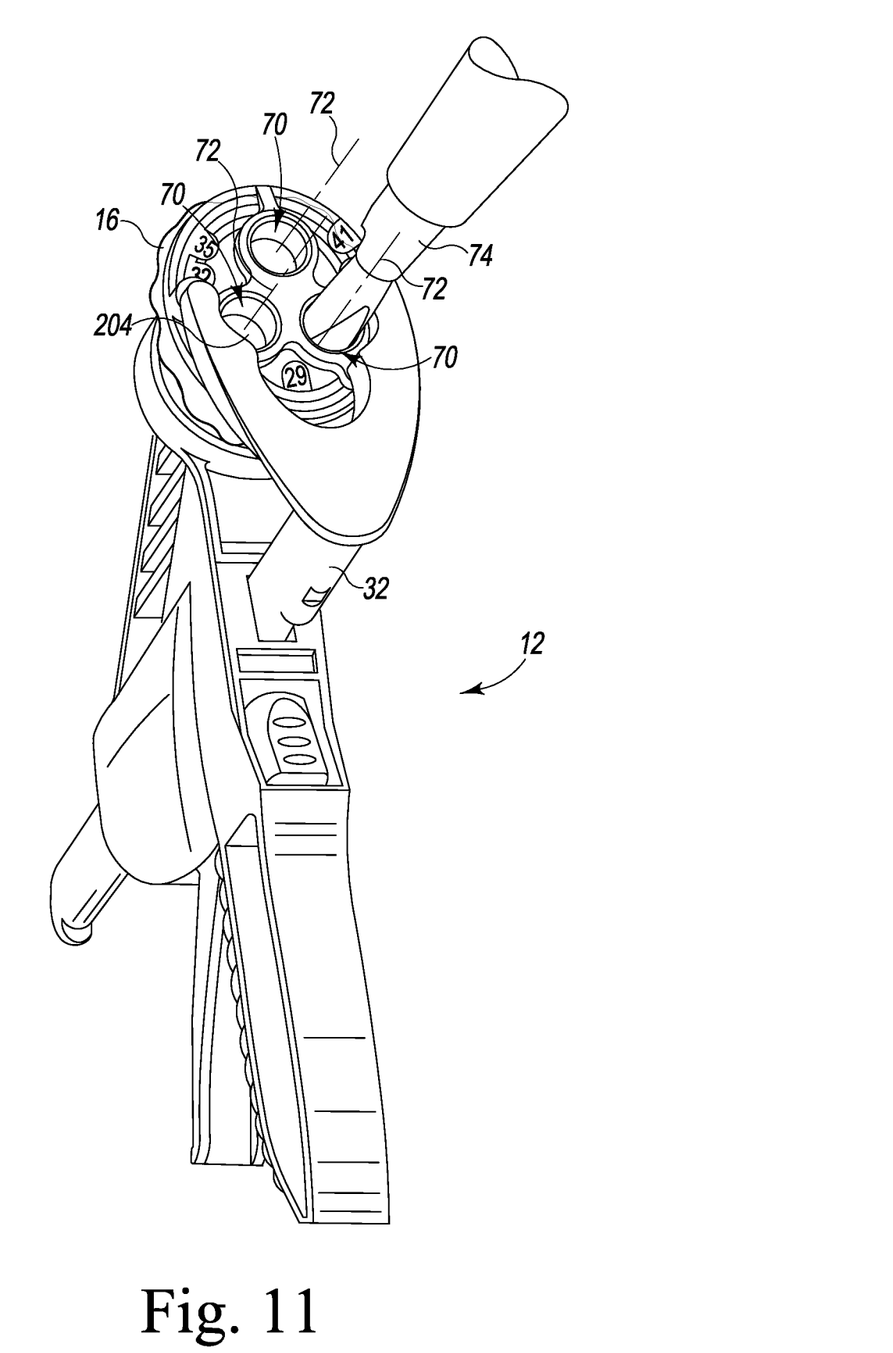
FIG. 11 is a perspective view of the orthopaedic surgical instrument of FIG. 1 with a surgical drill.

After the surgeon has clamped the patient's resected patella 16 between the plates 34, 38 of the guide 12, the resected posterior surface 204 of the patella 16 is surgically-prepared to receive the patella prosthetic component 18. As shown in FIG. 11, the surgeon may drill a series of pilot holes in the surface 204 that correspond to the position of a number of mounting pegs 210 of the component 18. To do so, the surgeon may insert a surgical drill 74 into each of the guide holes 70 defined in the drill plate 38. The drill 74 is advanced along the axis 72 through the guide hole 70 and into contact the surface 204. The surgeon activates the drill 74 and advances the drill 74 along the guide hole 70 until a pilot hole of sufficient depth is formed in the patient's resected patella 16. The surgeon may then repeat the drilling operation through each of the guide holes 70 until the required pilot holes are created. At any time, the surgeon may actuate the release button 142 and manually unclamp the patient's resected patella 16.

After pilot holes are created in the resected posterior surface 204, the surgeon may position the patella prosthetic component 18 for attachment to the patient's resected patella 16 and apply cement to the anterior surface 212 of the component 18. After the component 18 is positioned over the patient's resected patella 16, the pegs 210 may be advanced into the pilot holes formed in the resected posterior surface 204 until the anterior surface 212 is placed into contact with the surface 204. The compression gasket 14 may be attached to the drill plate 38, thereby covering the teeth 62 extending outwardly from the clamping surface 56. In that position, the gasket 14 is positioned between the drill plate 38 and the component 18.

Figure 12:
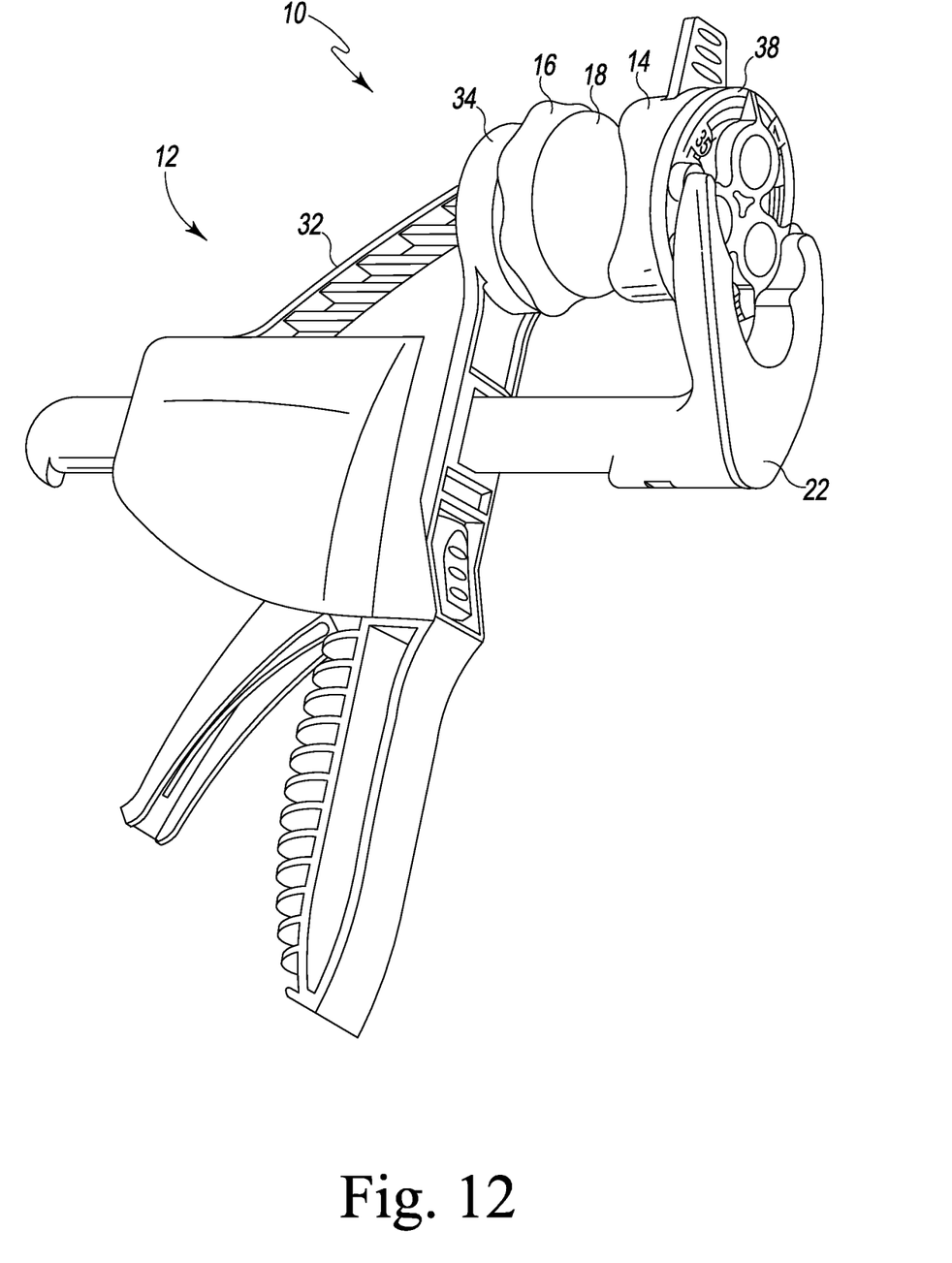
FIG. 12 is a perspective view of the orthopaedic surgical instrument of FIG. 1 with a patella prosthetic component secured to the patient's resected patella.

The surgeon may again operate the clamp actuation mechanism 42 to clamp the component 18 to the patient's resected patella 16, as shown in FIG. 12. To do so, the surgeon may squeeze the lower lever arm 102 to apply a predetermined amount of force to the trigger arm 44 to move the drill plate 38 and gasket 14 toward the mounting plate 34. The compression gasket 14 is advanced into contact with the posterior bearing surface 214 of the component 18, and the component 18 is seated within and stabilized by the concave surface 182 of the gasket 14 such that the component 18 is clamped firmly to the patient's resected patella 16 until polymerization is complete and the component 18 is secured to the patient's resected patella 16.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, the gasket 14 may be omitted from embodiments of the instrument 10 where, for example, the teeth of the drill guide are removable or omitted.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument, comprising:
   a patella drill guide that comprises (i) a first bracket including a mounting plate having a first clamping surface with a first plurality of teeth extending therefrom, and (ii) a second bracket moveably coupled to the first bracket, the second bracket including a drill plate having a plurality of guide holes defined therein, each of the plurality of guide holes being sized to receive a surgical drill, and
   a gasket removably coupled to the second bracket, the gasket being configured to cover the plurality of guide holes when coupled to the second bracket,
   wherein (i) the drill plate is formed from a substantially transparent material, (ii) the drill plate includes a first clamping surface facing the first clamping surface of the mounting plate, and (iii) the first clamping surface of the drill plate has a second plurality of teeth extending therefrom.

2. The orthopaedic surgical instrument of claim 1, wherein the first clamping surface of the mounting plate extends substantially parallel to the first clamping surface of the drill plate.

3. The orthopaedic surgical instrument of claim 1, wherein the gasket has a first surface configured to contact the first clamping surface of the drill plate, the first surface of the gasket having a plurality of positioning holes defined therein that are configured to receive the second plurality of teeth of the drill plate.

4. The orthopaedic surgical instrument of claim 3, wherein the gasket has a concave second surface opposite the first surface.

5. The orthopaedic surgical instrument of claim 1, wherein the first clamping surface of the drill plate has a plurality of etch marks defined therein, each etch mark corresponding to a size of a patient's patella.

6. The orthopaedic surgical instrument of claim 5, wherein the plurality of etch marks are arranged as a plurality of inscribed lines defined in the first clamping surface of the drill plate.

7. The orthopaedic surgical instrument of claim 6, wherein
   the drill plate has a front surface positioned opposite the first clamping surface, and
   each inscribed line is visible through the front surface.

8. The orthopaedic surgical instrument of claim 1, wherein the mounting plate and the drill plate are formed from a polymeric material.

9. The orthopaedic surgical instrument of claim 8, further comprising a plurality of metal bushings attached to the drill plate, each metal bushing defining a corresponding one of the plurality of guide holes.

10. The orthopaedic surgical instrument of claim 1, wherein the plurality of guide holes of the drill plate are arranged in a triangular pattern.

11. The orthopaedic surgical instrument of claim 1, wherein the gasket is formed from an elastomeric material.

12. An orthopaedic surgical instrument, comprising:
a housing including a handle and a first bracket, the first bracket having a mounting plate and a plurality of teeth extending therefrom,
a second bracket moveably coupled to the housing, the second bracket having (i) a drill plate spaced apart from the mounting plate of the first bracket and including a plurality of guide holes, each of the guide holes being sized to receive a surgical drill and having a longitudinal axis extending therethrough, (ii) a plurality of teeth extending from the drill plate toward the mounting plate, and (iii) a beam moveably coupled to the housing, the beam being configured to move relative to the housing along an axis extending parallel to the longitudinal axes of the guide holes, and
a clamp actuation mechanism coupled to the housing and the second bracket, the clamp actuation mechanism being operable to move the second bracket in a first direction toward the first bracket, the clamp actuation mechanism including (i) an actuation plate positioned in the housing and configured to engage the beam, the actuation plate including a follower surface, and (ii) a lever pivotally coupled to the housing such that the lever is moveable between a first position and a second position, the lever including a cam surface configured to engage the follower surface of the actuation plate when the lever is moved from the first position to the second position such that the actuation plate engages the beam to move the second bracket along the axis in the first direction.

13. The orthopaedic surgical instrument of claim 12, wherein the clamp actuation mechanism includes a biasing element positioned between the actuation plate and an inner wall of the housing.

14. The orthopaedic surgical instrument of claim 12, further comprising a locking mechanism configured to selectively prevent movement of the second bracket in a second direction away from the first bracket.

15. The orthopaedic surgical instrument of claim 14, wherein the locking mechanism comprises
a locking plate moveable between (i) a first position in which the locking plate engages the beam to prevent movement of the second bracket in the second direction, and (ii) a second position in which the locking plate is disengaged from the beam such that the second bracket is permitted to move in the second direction, and
a biasing element positioned between the locking plate and the housing, the biasing element biasing the locking plate in the first position.

16. The orthopaedic surgical instrument of claim 15, further comprising a release button attached to the locking plate.

17. An orthopaedic surgical instrument, comprising:
a polymeric housing including a handle and a first bracket, the first bracket having a mounting plate and a plurality of teeth extending therefrom,
a second bracket moveably coupled to the housing, the second bracket having a drill plate formed from a substantially transparent material, the drill plate including (i) a clamping surface, (ii) a front surface, (iii) a plurality of guide holes extending through the clamping surface and the front surface, each of the guide holes being sized to receive a surgical drill, and (iv) a plurality of etch marks defined in the clamping surface of the drill plate, the plurality of etch marks being visible through the front surface,
a clamp actuation mechanism coupled to the polymeric housing and the second bracket, the clamp actuation mechanism being operable to move the second bracket in a first direction toward the first bracket, and
a locking mechanism coupled to the housing and the second bracket, the locking mechanism being configured to selectively prevent movement of the second bracket in a second direction away from the first bracket.

* * * * *